(12) United States Patent
Wang et al.

(10) Patent No.: US 10,485,414 B2
(45) Date of Patent: Nov. 26, 2019

(54) METHOD FOR OBTAINING EAR DRUM STANDARD IMAGE AND THE RELATED DESIGN OF OTOSCOPE AND SOFTWARE

(71) Applicant: SyncVision Technology Corp., New Taipei (TW)

(72) Inventors: Pa-Chun Wang, Taipei (TW); Te-Yung Fang, Taipei (TW)

(73) Assignee: SYNCVISION TECHNOLOGY CORP., New Taipei (TW)

( * ) Notice: Subject to any disclaimer, the term of this patent is extended or adjusted under 35 U.S.C. 154(b) by 45 days.

(21) Appl. No.: 15/830,035

(22) Filed: Dec. 4, 2017

(65) Prior Publication Data

US 2019/0099069 A1   Apr. 4, 2019

(30) Foreign Application Priority Data

Sep. 30, 2017   (TW) .............................. 106133945 A

(51) Int. Cl.
*A61B 1/00* (2006.01)
*A61B 1/227* (2006.01)
*A61B 1/06* (2006.01)
*A61B 1/04* (2006.01)

(52) U.S. Cl.
CPC .......... *A61B 1/227* (2013.01); *A61B 1/00009* (2013.01); *A61B 1/00066* (2013.01); *A61B 1/04* (2013.01); *A61B 1/0607* (2013.01); *A61B 1/00052* (2013.01); *A61B 1/00055* (2013.01)

(58) Field of Classification Search
CPC ......... A61B 1/227; A61B 5/6817; A61B 1/05; A61B 1/053; A61B 1/00009
See application file for complete search history.

(56) References Cited

U.S. PATENT DOCUMENTS

2015/0065803 A1* 3/2015 Douglas ............. A61B 1/00009
                                                                600/200

* cited by examiner

*Primary Examiner* — Julianna N Harvey
*Assistant Examiner* — Christina Negrellirodriguez
(74) *Attorney, Agent, or Firm* — Muncy, Geissler, Olds & Lowe, P.C.

(57) ABSTRACT

This invention provides a method for obtaining ear drum standard image and the design of related otoscope and software, which includes the following steps: First, moving an otoscope with a circle sight to a target position in ear canal, and capturing an ear drum image; Then, choosing an ear drum region from the ear drum image, and calculating an area overlapping between the circle sight and the ear drum region. If the area does not satisfy a standard value, moving the otoscope to another target position, and repeating above steps; otherwise, choosing the ear drum image to be an ear drum standard image.

1 Claim, 4 Drawing Sheets

METHOD FOR OBTAINING EAR DRUM STANDARD IMAGE AND THE RELATED DESIGN OF OTOSCOPE AND SOFTWARE

CROSS-REFERENCE TO RELATED APPLICATIONS

This Non-provisional application claims priority under 35 U.S.C. § 119(a) on Patent Application No(s). 106133945 filed in Taiwan, Republic of China Sep. 30, 2017, the entire contents of which are hereby incorporated by reference.

FIELD OF THE INVENTION

The present invention relates to a method for obtaining a medical image and an apparatus thereof, and more particularly, to a method for obtaining an ear drum standard image and an otoscope design thereof, and a non-transitory computer readable recording medium for executing the instruction.

BACKGROUND OF THE INVENTION

A series of middle ear inflammatory diseases is collectively called otitis media, which includes two most common diseases: acute otitis media (AOM) and acute otitis media with effusion (OME). Patients with acute otitis media may have fever and feel pain, and hearing disorders would usually be happened. However, if it does not completely be cured, the acute otitis media will be converted into otitis media with effusion or chronic suppurative otitis media, moreover, it will result in permanent damage to the ear drum, collapse, or cholesteatoma. Some studies showed that if young children have otitis media for a long time, they will cause problem of hearing impairment easily and reduce the learning ability.

The diagnosis of otitis media is usually depended on the medical staffs, who assess through ear mirror, endoscopy, visual inspection of the appearance of the ear drum, or patient behavior, and classify the type otitis media. For example, the clinical symptoms of acute otitis media include ear pain and other clinical symptoms. On the other hand, children often pull the ears, increase the crying frequency and have poor quality of sleep, or sometimes they would loss appetite or have fever. The symptom of acute otitis media with effusion is observation of liquid, which is not caused by infection, in ear over 3 months; Moreover, OME means ear inflammation has been more than two weeks, which would lead the ear began to suppuration, but this symptom could be caused by acute otitis media complications.

SUMMARY OF THE INVENTION

Currently, there is no any standard valuation process for evaluating ear drum images, which means the experience of medical staff is needed to control the process, so the misjudge often happens during initial inquiry. Therefore, the present invention provides a method for obtaining an ear drum standard image that can help medical staffs to diagnose ear inflammation, which comprises the steps of:
(a) moving an otoscope with a circle sight to a target position in ear canal, and capturing an ear drum image;
(b) choosing an ear drum region from the ear drum image, and calculating an area overlapping between the circle sight and the ear drum region;
(c) if the area does not suffice a standard value, moving the otoscope to a predetermined position by the difference of the repetition area, and repeating the steps (a) to (b), the standard value is established by a relationship of ear canal depth and ear drum location. It may provide clear ear drum image for capturing. Wherein the standard value is over 70%, preferably, the standard value is between 90% to 95%; and
(d) if the repeat area suffices a standard value, choosing the ear drum image to be an ear drum standard image.

In one embodiment, the circle sight has a marked area, such as a triangle keypad, in the step (d), the triangular keypad is used to parallel auditory canal to aim at an optimal target area on the ear drum before obtaining the ear drum image.

In one embodiment, in the step (b), the ear drum interval, which is between the edge of ear canal and the ear drum, is circled by the contrast of the ear drum image.

In one embodiment, the method of the present invention further comprises:
(e) comparing ear drum standard image with a plurality of the ear drum reference images from an otitis media database, and to assess whether the ear drum standard image has any corresponding feature of otitis media disorder media.

Moreover, the present invention present invention provides a non-transitory computer readable recording medium comprising a plurality of instructions, when a processor is connected to an otoscope, execute the instructions and obtain an ear drum standard image, wherein the instructions comprising:
(a) capturing an ear drum image in a focal length range of an otoscope;
(b) choosing an ear drum region from the ear drum image, and calculating an area overlapping between the circle sight and the ear drum region;
(c) if the repeat area does not suffice a standard value, moving the otoscope to another target position, and repeating the steps (a) to (b) the standard value is established by the relationship of ear canal depth and ear drum location; and
(d) if the area suffices the standard value, choosing the ear drum image to be an ear drum standard image.

Besides, the otoscope of the present invention comprising: a handle part, a detecting part and a display part.

The detecting part, which is fixed to the upper end of the handle part, is having a side fixedly coupled with an outwardly tapered detecting part, and is having an image capturing module extending to the distal end of the detecting part for capturing an ear drum image in a focal length range of the otoscope and an ear drum standard image.

The display part, which is connected to the detecting part, is having a circle sight which is circled an ear canal in an ear drum image, and calculating an area overlapping between the circle sight and the ear drum region, if the area does not suffice a standard value, moving the otoscope to another target position, provide an error display.

In one embodiment, the otoscope of the present invention further comprises a step motor and an otitis media database.

The step motor, which is connected to the detecting part and display part, is moving to the predetermined position by the difference value of the area when the error display occurs.

The otitis media database, which is connected to a camera module, is saving a plurality of the ear drum reference images, and is to assess whether the ear drum standard image has any corresponding feature of otitis media.

DETAILED DESCRIPTION OF THE INVENTION

By ways of illustration, the specific embodiments will be disclosed in detail below, however, the features of the invention are not limited to these embodiments.

Figure 1:
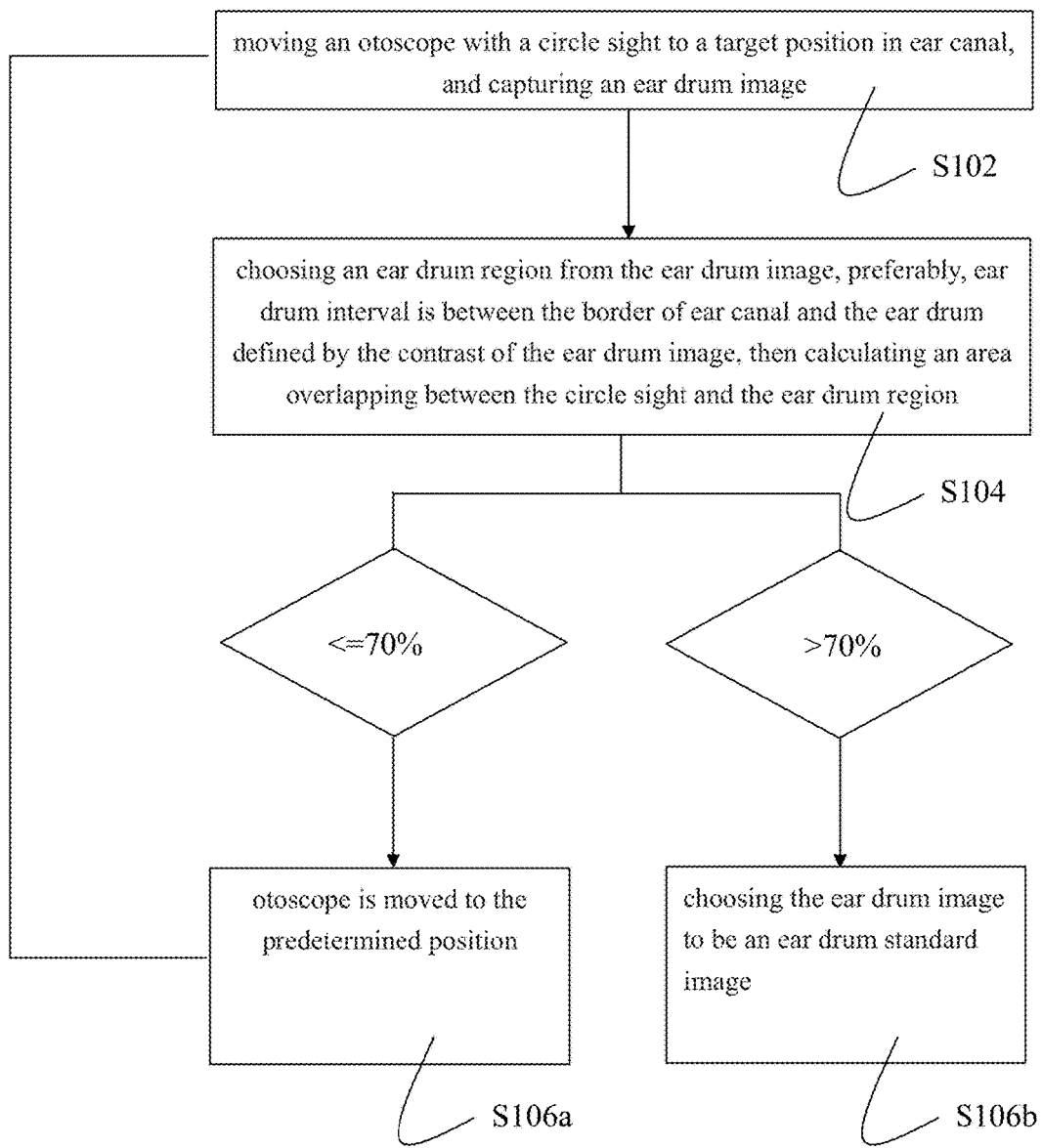
FIG. 1 is a flow chart showing a method of obtaining an ear drum standard image of the present invention.

Please refer to FIG. 1, which is a flow chart showing a method of obtaining an ear drum standard image of the present invention, comprises the steps of (a) moving an otoscope with a circle sight to a target position in ear canal and capturing an ear drum image S102;

The ear canal has a fixed length range, the adult ear canal is about 2.5 to 3.5 cm usually, and the child ear canal length is half to one-third of adult ear canal length. In order to avoid hurting the ear drum, the distance between the otoscope and ear drum should be noticed during image capturing. The most appropriate distance is when the ear drum is located in the otoscope focal length interval, which will make the resolution of ear drum image enough to be identified by the naked eye.

(b) choosing an ear drum region from the ear drum image, preferably, the ear drum interval, which is between the edge of ear canal and the ear drum, is circled by the contrast of the ear drum image, then calculating an area overlapping between the circle sight and the ear drum region S104.

Figure 2A:
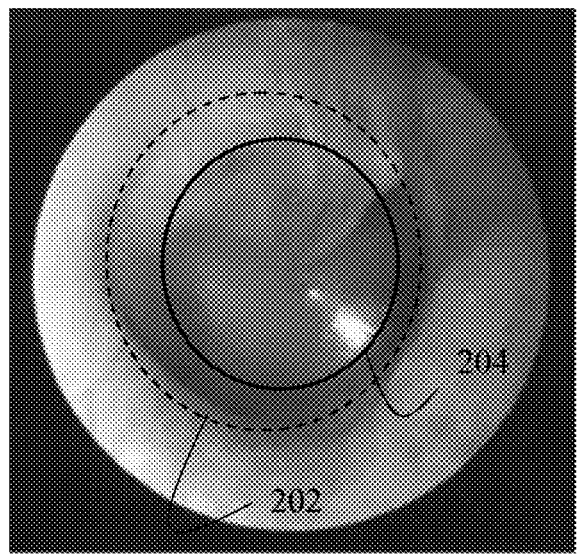
FIGS. 2A and 2B illustrate a schematic diagram showing the contraposition of the ear drum image captured by the present invention with the circular sight.

Please refer to FIG. 2A, the coverage of the circular sight 204 shows whether the captured ear drum image is deviated from the center, and whether the distance between the otoscope and the ear drum is in appropriate focal plane; the standard value is 70% above of the area of ear drum interval 202 and the circle sight 204, preferably. In one of the best embodiment, the standard value is 90% above of the repeat area of ear drum interval 202 and the circle sight 204. Therefore, if the area does not suffice a standard value, moving the otoscope to another target position manually or mechanically by the reminder of the captured image, which comprises the steps of;

(c) If the repeat area does not suffice a standard value, moving the otoscope to another target position, preferably, the otoscope is moved to the predetermined position by the difference of the repetition area, and repeat step (a) to (b) until the repeat area satisfy the standard value S106a; (d) if the repeat area suffices the standard value, choosing the ear drum image to be an ear drum standard image S106b.

Figure 2B:
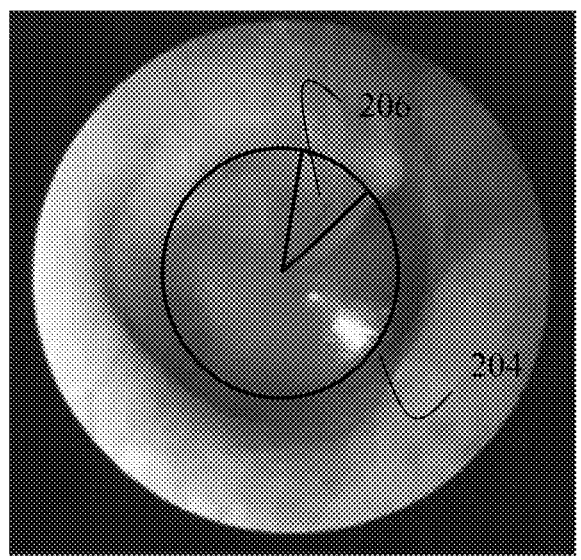

Please refer to FIG. 2B, the ear drum and middle ear are connected by three ossicles to form a sequence of mechanical systems to achieve the effect of amplifying the sound. The clinical image obtained from the appropriate focal length can clearly identify the fixed anatomical position behind the ear drum. The position of the three auditory small bones was used as the reference to identify the ear drum imaging belongs to the left ear or right ear. In one of the best embodiment, the circle sight 204 has an anatomic landmark 206 such as a triangular keypad, in the step (d), the anatomic landmark 206 is used to parallel the auditory canal to aim at an optimal target area on the ear drum before obtaining the ear drum image.

It is possible to achieve the purpose of capturing an accurate and consistent ear drum image through the method of the present invention. In addition to the simple operation of the otoscope, the medical personnel can also establish the database by scandalization of the ear drum standard image. The risk of misdiagnosis can be reduced through the ear drum image comparison database. Wherein the method further comprises the steps of: (e) comparing the ear drum standard image with a plurality of the ear drum reference images from an otitis media database, and to assess whether the ear drum standard image has any corresponding feature of otitis media.

Figure 3:
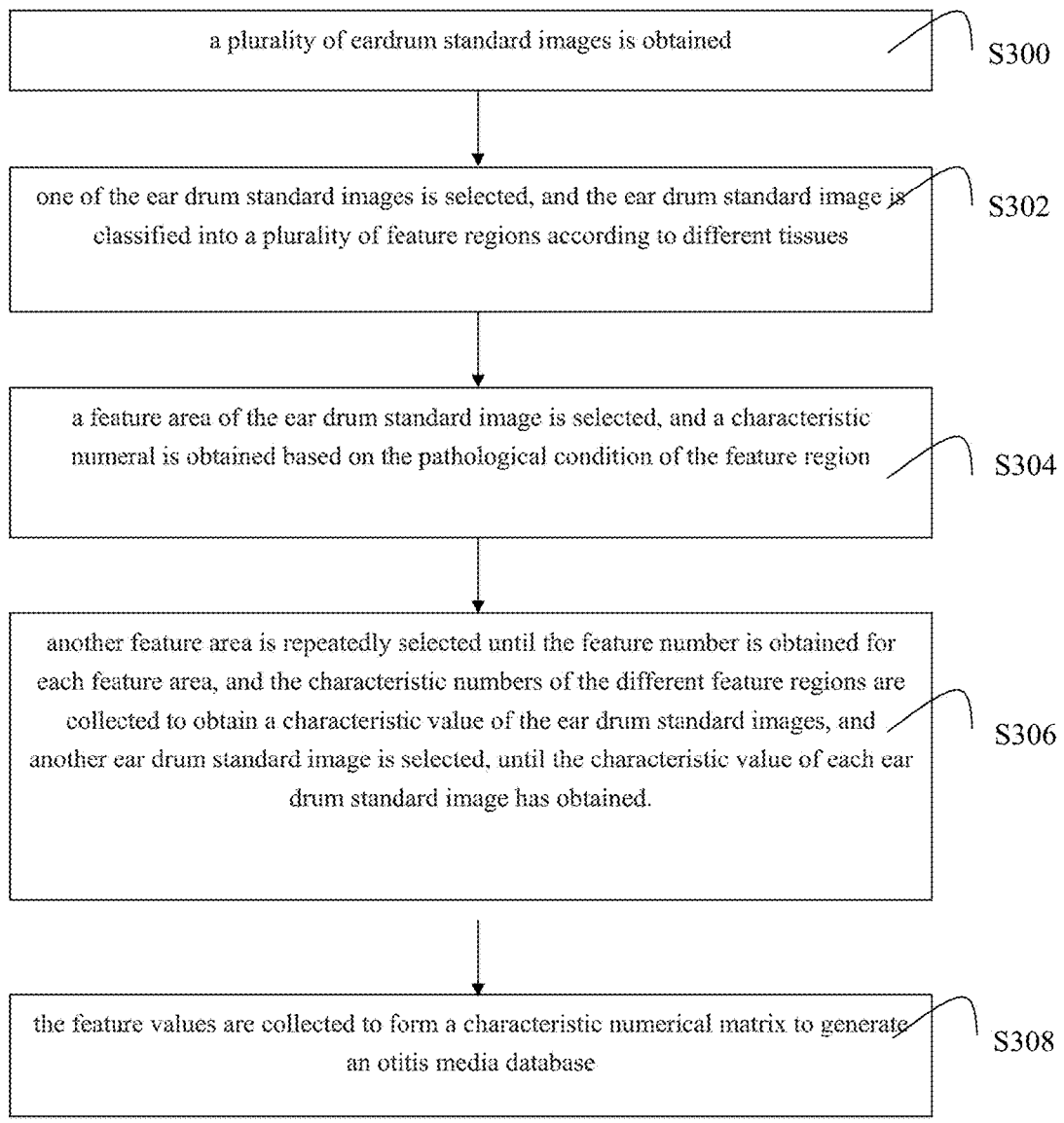
FIG. 3 shows a flow chart to reveal the establishment method of otitis database.

Please refer to FIG. 3, which is one of the best embodiment of the present invention, the otitis media database can be established by the following steps: first, in step S300, a plurality of ear drum standard images is obtained, which includes an acute otitis media and an image of OME. Next, in step S302, one of the ear drum standard images is selected, and the ear drum standard image is classified into a plurality of feature regions according to different tissues. In step S304, a feature area of the ear drum standard image is selected, and a characteristic numeral is obtained based on the pathological condition of the feature region. Next, in step S306, another feature area is repeatedly selected until the feature number is obtained for each feature area, and the characteristic numbers of the different feature regions are collected to obtain a characteristic value of the ear drum standard images, and another ear drum standard image is selected, until the characteristic value of each ear drum standard image has obtained. Finally, in step S308, the feature values are collected to form a characteristic numerical matrix to generate an otitis media database.

Figure 4:
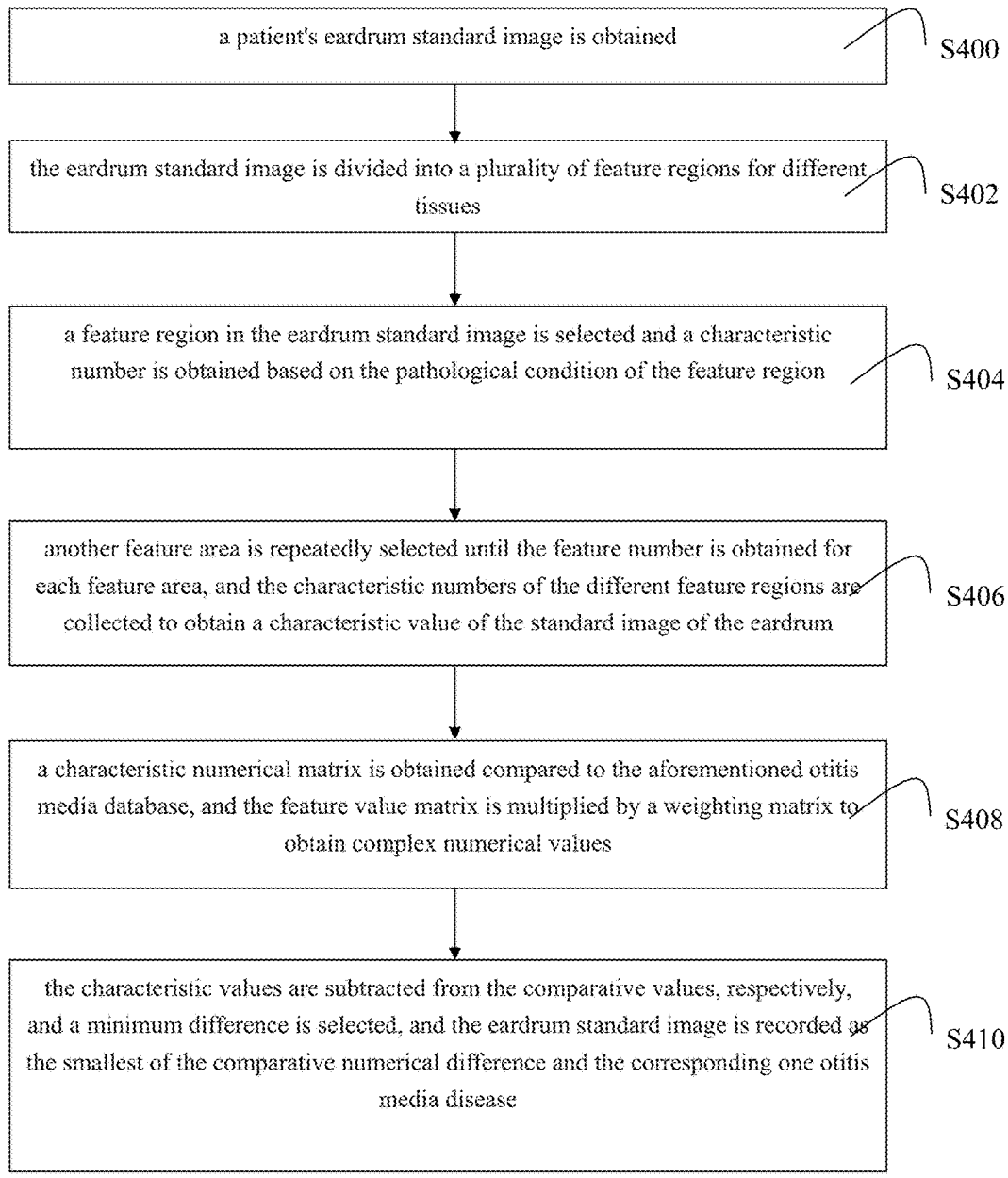
FIG. 4 shows a flow chart to reveal the assessment method of otitis media.

Please refer to FIG. 4, the otitis media disorder may be assessed by the following procedure in one of the embodiment of the present invention: First, in step S400, a patient's ear drum standard image is obtained. Next, in step S402, the ear drum standard image is divided into a plurality of feature regions for different tissues. In step S404, a feature region in the ear drum standard image is selected and a characteristic number is obtained based on the pathological condition of the feature region. Next, in step S406, another feature area is repeatedly selected until the feature number is obtained for each feature area, and the characteristic numbers of the different feature regions are collected to obtain a characteristic value of the standard image of the ear drum. In step S408, a characteristic numerical matrix is obtained compared to the aforementioned otitis media database, and the feature value matrix is multiplied by a weighting matrix to obtain complex numerical values. Finally, in step S410, the characteristic values are subtracted from the comparative values, respectively, and a minimum difference is selected, and the ear drum standard image is recorded as the smallest of the comparative numerical difference and the corresponding one otitis media disease.

Wherein the aforementioned feature region comprises at least a color feature, a geometric feature, a tissue feature, or a shape feature. Wherein the color feature comprises a hue, a saturation, or a brightness; the geometrical feature comprises a directional gradient histogram, wherein the tissue feature comprises a local binary pattern; and the shape feature comprises a self-similar geometric pattern.

According to the method of the present invention, the steps of the method can he written in a software program, stored in any recording unit of a microprocessor, or an article and a device containing the above-mentioned recording medium(MO), IC chip, random access memory (RAM), or any other device having above-mentioned recording unit known by the skilled person. The execution of the processor of the present invention may be selected from a computer, a tablet computer, a handset, a palmtop computer, a personal digital assistant (PDA), and other devices having input and output functions.

According to the present invention, a non-transitory computer readable recording medium comprising a plurality of instructions is provided, and when a processor is connected to an otoscope, the instructions are executed to obtain an ear drum standard image, and the instructions include: (a) capturing an ear drum image in a focal length range of an otoscope; (b) choosing an ear drum region from the ear drum image, and calculating a repeat area between the circle sight and the ear drain region; (c) If the repeat area does not suffice a standard value, moving the otoscope to another target position, and repeating the steps (a) to (b); (d) If the repeat area suffices the standard value, choosing the ear drum image to be an ear drum standard image.

Moreover, the present invention provides a method for obtaining an ear drum standard image by a recording medium, the present invention being capable of embedding a working firmware in an otoscope, and directly applying the aforementioned instructions to the otoscope, the structure comprises: a handle part, a detecting part and a display part; wherein a detecting part, which is fixed to the upper end of the handle part, is having a side fixedly coupled with an outwardly tapered detecting part, and is having an image capturing module extending to the distal end of the detecting part for capturing an ear drum image in a focal length range of an otoscope and an ear drum standard image; a display part, which is connected to the detecting part, is having a circle sight which is circled an ear canal in an ear drum image, and calculating an area overlapping between the circle sight and the ear drum region, if the repeat area does not suffice a standard value, moving the otoscope to another target position, provide an error display.

Moreover, the otoscope of the present invention comprises a step motor and an otitis media database; wherein the step motor, which is connected to the detecting part and display part, is moving to the predetermined position by the difference value of the repeat area when the error display occurs. The otitis media database, which is connected to a camera module, is saying a plurality of the ear drum reference images, and is to assess whether the ear drum standard image has any corresponding feature of otitis media.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

SYMBOLS

Steps of capturing an ear drum image S102~S106
Ear drum interval 202
Circular sight 204
Anatomic landmark 206
Establishment steps of otitis database S300~S308
Assessment steps of otitis media S400~S410

What is claimed is:

1. A non-transitory computer readable recording medium comprising a plurality of instructions, when a processor is connected to an otoscope with a circle sight, execute the instructions and obtain an ear drum standard image, wherein the instructions comprising:
    (a) capturing an ear drum image in a focal length range of the otoscope in a target position;
    (b) choosing an ear drum region from the ear drum image, and calculating a repeat area between the circle sight and the ear drum region;
    (c) if the area does not suffice a standard value, moving the otoscope to another target position, and repeating the steps (a) to (b);
    (d) if the repeat area suffices the standard value, choosing the ear drum image to be an ear drum standard image, wherein the otoscope comprises:
        a handle part;
        a detecting part, which is fixed to the upper end of the handle part, is having a side fixedly coupled with an outwardly tapered detecting part, and is having an image capturing module extending to the distal end of the detecting part for capturing the ear drum image in the focal length range of the otoscope and the ear drum standard image;
        a display part, which is connected to the detecting part, is having the circle sight which is circled an ear canal in the ear drum image, and calculating the repeat area between the circle sight and the ear drum region, if the repeat area does not suffice the standard value, moving the otoscope to another target position, provide an error display; and
        a step motor, which is connected to the detecting part and display part, is moving the otoscope to another target position by a difference value of the repeat area when the error display occurs.

* * * * *